United States Patent [19]
Amaral et al.

[11] Patent Number: 5,849,581
[45] Date of Patent: Dec. 15, 1998

[54] REGULATORS OF UCP3 GENE EXPRESSION

[75] Inventors: M. Catherine Amaral; Ning Zhang; Jin-Long Chen, all of S San Francisco, Calif.

[73] Assignee: Tularik Inc., S San Francisco, Calif.

[21] Appl. No.: 948,277

[22] Filed: Oct. 9, 1997

[51] Int. Cl.$^6$ ................ C12N 5/10; C12N 1/00; C12N 15/11; C12N 15/63

[52] U.S. Cl. ............... 435/325; 435/243; 435/320.1; 435/410; 536/23.1; 536/23.5; 536/24.1

[58] Field of Search ................ 536/23.1, 27.1, 536/23.5; 435/325, 320.1, 410, 243

[56] References Cited

PUBLICATIONS

Boss et al, FEBS Letters, vol. 408, No. 1, pp. 39–42, May 12, 1997.

*Primary Examiner*—Terry Mickelvey
*Attorney, Agent, or Firm*—Richard Aron Osman

[57] ABSTRACT

The invention relates to regulators of UCP3 gene transcription, including novel UCP3 transcriptional promoters. UCP3 gene promoters are used in diagnosis and pharmaceutical development. In particular, transfected cells comprising UCP3 gene promoters operably linked to a reporter are used in high-throughput pharmaceutical screens.

19 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AAGCTTTGCA  CTTGAACATC  CATGCTTCTG  ACCACCTGCC  CTGTGACGCT  GGCTCTGTGC        60

CCCAGTCCAG  AAAAGACTTC  TGCCTACTCC  TCCTCTGCCC  TACCCAGTTA  ACTCCCTTTC       120

CTTCCCTCCC  TTCTGCTTCT  CACTCCTCCC  CTCCCTTCTC  TTCTTCTTCT  CCCCTTCCCC       180

CATCACCTGG  GGCCCGATTC  AGCTGTGCCC  AGCCCTTACT  CTGAGTGCCC  ACAGATGGAG       240

CCTCCAGTAG  CTTCTGTGGG  GCACCCTTCC  ACCAGGTCCC  AGCTCCCTTG  GCTCCAGCAG       300

TGTCCATGCT  AAAGCCTCCA  AGTGTCATGT  TGGAGAGAAT  GGTGTTCACA  GTAGATAAGC       360

CCAAAATGCC  TTACAGTTTA  CAGGCTGGAG  TCAGGCCCCG  CCACGTTGCT  GGCTACATGA       420

CTTCCCTGAG  ATTCCATTTC  CTCCTCAGTA  AAATAAGTGG  TAAGATTTTA  GGATCCCAG       480

CACTAAAAAG  AAACGAAATA  CTGATACAGG  CTCCAACATG  GATGAATTTT  GAAAGCATTA       540

CTATACTAAG  TGAAAGAAGC  CAGTCACAAA  CAAGCACATA  TTGGATGATT  CCATTTCTAG       600

GAAGTGTTCA  GAACAGGCAA  ATTTATAGAG  ACAGAAAGTA  GATTGATTAG  TGGTTGCCTG       660

AGGCTGGGGA  GCGGGGAAG   GGAGGTGACT  ACCAATGTGT  ATGGAGTTTT  TCCAGGGTGA       720

GAGGGTGATG  AAAATGTTCT  AAAATAGATT  GTGTTGATGG  TTGTGCCACT  CAGAATATAC       780

TAAAAACCAT  TTGAATTGTG  CACTTGAAAC  AGATGAATTG  TACGGTATGT  GAATTCTATA       840

TCAATAAATC  TGTAATTTAA  AAAAAAAAA   TTAGGTCGGG  TGCAGTGGCT  CACACCTATA       900

ATCCCAGCAC  TTTGCCAGAC  TGAGGCAGGA  GGATCACTTA  AGCCCAGGAG  TTCAAGACCA       960

GCCTGGGGAA  CACAGCAAGA  CCTCGTCTCT  ACTAAAAAAT  TTTAAATTAC  AAAAAAAAA      1020

AGTAAAAAAA  ATAGAATCCT  AATAGTACCT  ATCTCATAGG  ATTGTGGAAA  ATAGTAGTAA     1080
```

| | | | | | | |
|---|---|---|---|---|---|---|
| TGTATGTAAA | ATATTTAGCA | CATAGTAGGC | ACAAAGAAAT | GACATTATTA | TTAAGAGACC | 1140 |
| TGGGAGAGCT | GTGCCCAGCC | TATCGTGGGA | GGCCTTGACC | TTTGGACTCA | AAAGTGGCAG | 1200 |
| CAGGTCCACC | CCCCCATACA | CCCTTGTCAC | CAAGGAAGCG | TCCACAGCTT | AAAGGAGCTA | 1260 |
| TATTAAAGCA | CCCCAAGTCA | AGAGGACTGA | ACCAGATCTG | GAACTCACTC | ACCTCCCCTC | 1320 |
| TCACCTCACT | GCCCTCACCA | GCCAGCCTCT | TGTCAAGTGA | TCAGGCTGTC | AACCAACTTC | 1380 |
| TCTAGGATAA | GGTTTCAGGT | CAGCCCGTGT | GTATAAGACC | AGTGCCAAGC | CAGAAGCAGC | 1440 |
| AGAGACAACA | GTGAATGACA | AGGAGGGGCC | ATCCAATCCC | TGCTGCCACC | TCCTGGGATG | 1500 |
| GAGCCCTAGG | GAGCCCCTGT | GCTGCCCCTG | CCGTGGCAGG | ACTCACAGGT | AAGACCGGTT | 1560 |
| TCTCCTCCCT | CATCCCTTCC | CCTCTCCCTC | TCCCTTCTCC | TTGTTCTCCC | TTTCATTGGA | 1620 |
| GGCTTTCAGA | GAGCAGCCCC | GAGCAGTCAG | GGCTCACTAG | CTGCAGCTTG | TCAGACCTGA | 1680 |
| TAGAGATTCA | GTCCAGCCGC | CACCTTATGA | AAAGGGAGCT | GTGGCCTTGA | TGAGGGTACT | 1740 |
| GTGGCAGGGC | TGGGGCTTGA | ACCCAACACC | CGTGTCACTC | ACTCAAGACT | CACACCCCCT | 1800 |
| TTGCCTTGCT | GGCTGCCTCT | GGTGGGATTT | TGCAAATCCC | CATAGACAGG | AAGTGGCTTT | 1860 |
| CTTCTTTGCC | TGCCCCAGAA | TCTCTGCGAT | TCCTCCAGAG | CATAAATCCC | TCTCTTTCCA | 1920 |
| TGAGGACCCT | GGGGCCCTCT | TCCTGAGTAG | GGATGACAGG | GGCACTTCTG | ACCTGAGGCG | 1980 |
| TGGTCCAGGT | CATTTGCTGG | | | | | 2000 |

(2) INFORMATION FOR SEQ ID NO:2:

(i) SEQUENCE CHARACTERISTICS:
        (A) LENGTH: 5436 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| ACTAGTGACC | CAAAAGATCT | GTCTATAGCT | ACAGCCAGAG | CACCGAATGG | GACAAGTATC | 60 |
| CTCTAAACAC | CAAAGATCTC | AGGATCTTGA | GATGAGGCAC | ACAGAAGCTT | AAAAGTCTCT | 120 |
| CAGAGAACCC | AAAGGGTATA | TCCACAGTAG | ACCACTACCA | TTGGTTCTAG | TGGAATGAAT | 180 |
| GAGGCATTTA | CTGCAGAGGC | AGTCTCCTTC | CAACCTGATC | TAAACCAGAT | CTTCATGACC | 240 |
| CAGTCCTACC | CATTCACTGG | TCTCATAGCA | TCCGAGCCCT | CGTCTTGACC | TGGCCTGCCC | 300 |
| GGGGTTGTGT | ATTGAAGCTC | TAGTTCATGC | CCTCAGAAGT | GCCTGGTCTG | GAGCAGAGGG | 360 |
| CAATATGGAC | ACTGGCCTCT | TGGCCCTCCC | CTGGCCTGAG | GTGTTACTTT | AGAAGGAAGA | 420 |
| ACTGTGAACC | AAAAACAACA | CCCTTCCTGT | TAGCCTAGAC | CTCCCCAGAA | CACAGAGCTG | 480 |
| TACCTCCAGG | CTCTGCCAAG | CATCCTAGCT | TGACACTGCT | TATTCTTGGC | CACCAGGAAG | 540 |
| GCTTGCCTAA | GGGCCTGCTC | GGCTTGCCCA | CCTCCCCCTC | AGTGCTTAGA | GATCTGGACT | 600 |
| GACAGGGATA | GTCCTGACTA | TTTGCCCAGC | CCCCTTGGCC | ATGGTTAGGA | AACTAGCACC | 660 |
| CAAGCAGCAG | AGAGGACACA | AGCTCATTCC | CCTTACCCCA | TTCTTTGGGT | AGGTCACTGT | 720 |
| GTCTTGCCTG | TTTTACTCTG | AGCTGTGAAG | CCAGGATCTG | CTGTCATTTC | TGCCTCCTGT | 780 |
| TGACGTGTAT | TGTTCTATAA | AAAGGAATAA | TGGGATTTCT | AAGTGTGCTC | ATCCTTGACC | 840 |
| CTCTCTAGCC | AGGCCTGACC | TTTCTTGTTA | GCAGGCTCAC | GGGGTACAAG | CTGGAGAGGT | 900 |
| GGAACAGTGT | ATTAGGGTCC | GTCAGCATGG | GAACAAAAAA | GATCTACCGG | CCTGTGGGGA | 960 |
| CAGCCTCCGT | TTCTTTCTGC | ACTGGCTCTT | CCTGCCTGGC | CTCCATCTCT | TTCCTAGGGG | 1020 |
| CCTCATTCTC | AGCCCACCAG | GCAACTTTGC | TATGTAGATC | TGAGCCCTTC | AGCACAGGAA | 1080 |

```
CCTGACAAGA  TACCAAAAAG  GGGAAAGTGG  CTGAGCACAC  GGCTTTGTCT  ATGGTAGCTG  1140
CTCAAGTGGG  ATTTCCACCT  GCCTCAGCTC  TGCCACTCAG  AGCTGCACGA  CCTTGAACTA  1200
ACTAAGTGCA  CCTGACCTTG  TGATGTCATG  GCCAGGGTTC  CACAAGACAG  GGTGTATGAG  1260
GTATTTGCAA  ACCAGGGACC  TAGAGAAAAT  GTTAGCCCAA  GGACCAGACT  CGCCTCTGCA  1320
ATGCTGTATC  CTCAGGACTA  ATCTAGATGA  CTTCCTTCTC  TCCAGGACAA  GAGTGAAGCC  1380
CACCAGGGGG  AGCCCTTGCC  CAGAGGCCTT  GTCGCCCCAG  ACCTTACTCC  ATCCCTCCCA  1440
ACCTTCCTGA  GGAAGAGACT  CGCAGGATTG  CACGGATATT  TTCTTCCCAG  TATTCCAAAA  1500
AGACTGAGGA  AACCTGAGGG  ACGTGGCTAC  CAGCCAGCCT  CTCAGCTCTG  TAAAGCTTGC  1560
AAGAGACAAC  AGGCCTATTT  CCCTCAGCAT  CCTCAGGCCA  CTAGCATCAC  CCTATTCCAT  1620
GGGTATCTTG  AGACCTAATC  AGCTAAGACC  AGAGGAGTGT  CCCAAACCAC  CTAGCAGCTG  1680
CCTACCAGGA  CCTCAGCTTC  CTTCTGTAAT  GAGGTGACTG  CTGGAAGTGA  GACTCAAGCA  1740
CCCAAGTGTC  CCACCCATCT  TCTGACTGTG  GGGCCTAAGG  AGGCCTCTCT  GAGCAGAGAA  1800
ACCAGTGTCC  TTGACACAGC  CTACTGCTGA  CCAGAGCCCA  CCTTCTGCTT  AAATAGGACA  1860
GGCTATTTTT  GCCATAAATA  TTGGAAGAAA  CATGGAATAA  GTATGTACAT  AGCTGAGAAA  1920
ATTCCAGAGC  CCTGTCCAGC  TTGTTTGTTT  GGGAATGAGG  TATTTTATTG  ATATAAATTA  1980
TTTTTATGAT  GTATTAATCA  ATAGAACAGG  GGAATTGCCT  CCTTTAAAAC  TGTATTCGGT  2040
TGTCTGAAAT  TTAACCATGT  TTTTAACATA  ATGTTTGTTT  CTACTCAGCT  CTGAAATTCA  2100
TTGCTCTTGC  CTTTGTTTTT  AATAAAGTC   TGGCATTTGT  ATTTGTGTAC  AAGTGTTTTT  2160
TGGGTTGGTC  ACTGGGAAAA  GGTGTTGCAG  AAAGAAGGAT  ACAGCCATCA  CTCCACCACC  2220
TGCAACATGA  GTCGCCATGA  GACTTGCTAG  TTCTTCCAAC  TGTCAGATTG  ACCCATGTTA  2280
GAGGGATGCT  AGTGTTCCAC  TTCTGGTGGT  TTGGGCTTTT  GCTTGCTTGC  TTGGTTTGTC  2340
TTTTCCTCTG  ATGGCCCTTT  AAATCTTGCT  CAGCACAGTG  AGCGTCCAAC  TAAGATCTCG  2400
TCCCCGGTGT  GACTCACGAG  GGCACTTCTG  TCAGAACACA  GCCACTTGGG  CAGCTACCAT  2460
AGACAAAGTC  CTCTGAGGAT  AATCTGAACG  GAATAGATGT  CCAGTGCGTC  TGGTAGTGAG  2520
GCGGAAAGGA  GCTACCTGAG  GGCTCTGCTT  GTCACCCTGT  GTGTCATTTC  TCTAAATCCT  2580
CACAACTCTA  TGATGCCCCT  CCCACAATTA  CCCTCAACAC  CATGGAAGTC  GGATGCATTG  2640
CTTCTGTATC  GGTACAAAGT  GCATCAGGAC  CGAAGACATA  CCCCAGAGAT  AAGGACTCAG  2700
ACCAAAGCAG  GATACAGGCA  GTAAACGCCC  TGAATTCGGG  CGGTCTCAGG  CTGCTAAATC  2760
CAGGGAGGGA  TTTCTGGAAG  AAACCCGTAC  TGGGGTAAAG  CCCAGAGAAT  GGTATAGACC  2820
AGGTCATGGA  CAGCTGCAAA  GAGAACCAGA  GAATGTTCTG  GACCATATCA  GTGTCCAGCC  2880
TGGCTGAAAC  TGTGGCTCTG  GCCTCATCTG  GAAGGCACAG  ACACGTAGAC  TCTGGCTTCG  2940
TATGGTCGCT  GTGAAGATCA  AATGGGACAT  TTCTGAAAAT  GCTTCGCTGG  CATTTGGCAC  3000
ATAATGGAAG  CTTGAGAAAT  GTCAGCCCTT  CCCACTCTTC  CTAAGCACCG  GGGTGAATTA  3060
GAGGCAAGCT  CACTGGCTAC  CCAGAACGCA  GAGCACTCCA  GCCTCCCATA  AGGGCCATGA  3120
ACCTTCAGCC  AAACCTGCCC  CTCAGATCTC  TGTTCCTTGG  AGGTCACCTT  GCAAACCTGC  3180
CCAGTCCTTA  GCCAGGGGTT  CCCCTTGCCC  CAGGCCTTGC  CTTCGGCCAG  AACAGAGCTT  3240
CCAGTACCTG  GAGTTCCACG  TCCCTCGGGG  TAAGAAACTT  CTAGGTTCCA  AGCCTAAGGG  3300
GTAAAGCCTA  GGGTGAAGAA  GATCACTGCC  AAATCCTGAT  CCTGTAAATA  ACCTGAAGGA  3360
GTCAAGTGAG  AACAGGGCCA  CAGGAGGGCA  CGGGCTGCAG  ACAAGGTGAA  GGTCTGAGAC  3420
ACAGACGACA  TGCCCAATTT  GTTATTTACC  AGTCTCTCCC  AGTGATAGCT  CTGAGGCAAC  3480
```

```
TTGACTTGCC AAGTTGTACA ACACATTTGT CACCACAACC AGAATGAACC CTGACTTCCT    3540
TATGCATGCC CTCCACAGAT GCCTGGAAAG TATTTCTGGT GACCCAGAGA CTGTAGCAGC    3600
CAACCTTAAA ACTCCCAGCA GAGGTTTGAC TCTAGCTAGG CCTGAGCTCT CCTCCCTCTG    3660
GGTTTCTCCA GAACCTGCTG CCTCTAGTTT GACTTCTACT TGTAGCCCCA GCCCCACAT    3720
GGTTCCCACA GTCCTGCCCA TGTCCAGATT AATAGTTCCA GACTGAGCTC AAAGCAGTGA    3780
GCAGGTCCTG GTCCAAGAAA CAGGATAGAC AGTCTAGATG TCACAGCACC CACCCTGCCA    3840
TGGCGCTGCG CTCAAGTTCC AAAATGTCCT CTACCTTCTC TGTCCTACTT ATCTCCTCTC    3900
CCCTCTCCTT TTAGTTTCCC TTCTATGCCA CCTGGCTCCC AACTTCAGCT GTGCCCACCC    3960
AGTCTTTAAC CTCAGCGCCT GCAGATGGAC CAGCCTACAG TGGTTGCTGC AAGGGATTTT    4020
GCTCACCCTG CCCCATCTCC GGTCCAGCA TGTCCATGTC ATGAGGAATC AGGATTGCAG    4080
CTGATAGACC CAAAGTGTGG TATAGGTTAC AGGCAAGTCA GGCCTGCAGT GACCTAGCTG    4140
TCTGTCCTTG ACAGTCAGTT TTCTGTGTAA AGTAAGCATT GACACATGAG GGCTCTACAC    4200
AGTACGTCAG TGTCTACCGG TACAGTGCAG TGTGTTAACA CCACTGTGAA AGAAACCAGC    4260
CACAAGAGGC TATACATTCT ATATAATCCT ACTCAAACAA AGCATCTAGA ACAAGCAAAT    4320
TAAGAAGCAG AATAAAGACG AGTGGTTGCC TGAAGCTGGG GGAAGGGAAA GGGGGTGACT    4380
TGTTCTGTTT TTGTCTTTGA GCCATGATGA AAGTGTTCTG AACTAGCATG TAGTAGTTGA    4440
TCAACCAGAC TGTACTAAAC ACTATTGTGT GCTCTATGTG GGCAAATCAC ATGCTGTGTA    4500
CAAAACATCT GTTGTCCTTT GTTTTAAAT TTAGGATCCT GCTTCCTAGA GATGTGGGAA    4560
ATAGAAGCGC TGTGCCTGAA ATATCAAGCA TATCTTGGCA CCAAGATGTC CTCTACCTTC    4620
TCTGCCCCGT CTTCTCCTCT CCCCTCTTGA GAATGTCAGG CCTCTAAGAA GTGACACCTG    4680
TAACCATTGT ATAGGATCCT GGAGAGCCCC TGTCCTAAGA GACCTTGTCC TTTGGGCTCT    4740
CAAAGGTGAC AAATGCTGTC ACACACCTCC TGGCCACCAA GGTAGCTCTC CTCTTGAAAG    4800
CTCAAAGGAG CCACATTAAA GAGCCCCAGG TCACGGAAGC TAAACCAGAT CTGGAACTCA    4860
CTGGTCCCCT CCCCGCAGCC TGCCTCTTGT CAAGTGATCA GACTGTCAAC TAGCTTCTCA    4920
GAATTAGGTT TCAGGTCAGC TGGTGCACAG GGCCAGTGCC GAGCCAGGGA CAGCAGAGAC    4980
AACAGTGAAT GGTGAGGCCC GGCCGTCAGA TCCTGCTGCT ACCTAATGGA GTGGAGCCTT    5040
AGGGTGGCCC TGCACTACCC AACCTTGGCT AGACGCACAG GTAAGACCCC ATACTCTGCT    5100
CTCCTCTCCC TTTTTCCCTT CCATGGATGC TCACAGCCAG GAGCTTGCTG GGATCACTCA    5160
GCACTGCGTG AGAGACCGAG AGTGAGCCGG TCTAGCTCCC ACCTAGTAAA GATGAAGGAA    5220
CTGCAGGCCT GGGGAGGGCC TTGACTTCCA CATCTATGTG ACTCCTCACA ACTCCCGTGT    5280
TTTGCTGACT CCTCTGCTGG GATCTTACAA ATGCCAAATG AAAAGTGTCC CTCTCCTTTG    5340
GCCCAGGATC CCCACGGAGC ACAAAGCCCT CTCCAGCAAG GATCCTGGGG CCCTTCCTGG    5400
GTAAAAATAA TGAGGGCACT CTGGCCTGAA GCCTGG                              5436
```

REGULATORS OF UCP3 GENE EXPRESSION

FIELD OF THE INVENTION

The field of this invention is the transcriptional promoter of the UCP3 gene and its use in drug screening.

BACKGROUND

A mitochondrial protein called uncoupling protein (UCP1) is thought to play an important role in the body's regulation of energy utilization. Such regulation provides wide spread physiological controls including body weight, appetite, glucose metabolism, temperature, immune responses, etc.. Mechanistically, UCP 1 is thought to create a pathway that allows dissipation of the proton electrochemical gradient across the inner mitochondrial membrane in brown adipose tissue, without coupling to any other energy consuming process (for review, see Nicholis & Locke (1984) Physiol Rev 64, 1–64). Unfortunately, the role of UCP1 in physiologies such as body weight regulation in large adult mammals such as people, cattle, pigs, etc. is likely to be limited, since there is little brown adipose tissue in such animals.

UCP2 is a second, related uncoupling protein that is much more widely expressed in large adult mammals (see, e.g. Fleury et al. (1997) Nature Genetics 15, 269–272 and Tartaglia et al. (1996) WO96/05861). Consistent with a role in the regulation of energy utilization generally, and in diabetes and obesity in particular, the UCP2 gene is upregulated in response to fat feeding and maps to regions of the human and mouse genomes linked to hyperinsulinaemia and obesity. Accordingly, upregulators of this gene hold great therapeutic promise for these diseases. To provide regulators of UCP2 gene expression, we cloned the endogenous promoter of the human UCP2 gene and identified various deletion mutants having transcriptional regulatory activity (U.S. Ser. No 08/846,012, filed Apr. 25, 1997).

UCP3 is a third, related uncoupling protein also widely expressed in large adult mammals. Accordingly, upregulators of this gene hold great therapeutic promise for diseases such as hyperinsulinaemia and obesity. To provide regulators of UCP3 gene expression, we have cloned the endogenous promoter of natural UCP3 genes and identified various deletion mutants having transcriptional regulatory activity.

SUMMARY OF THE INVENTION

The invention provides methods and compositions relating to the UCP3 gene transcriptional promoter. The compositions include recombinant regulators of gene expression comprising the UCP3 promoter of at least one of SEQ ID NOS: 1 and 2, or a deletion mutant thereof at least 50 bp in length having cis transcriptional regulatory activity. Exemplary such deletion mutants comprise at lease one of SEQ ID NO:1, bases 411–460, bases 461–510, bases 401–563, bases 319–326, bases 98–104, bases 49–56, bases 49–104 and bases 547–554. In preferred embodiments, the regulators comprise at least one of a GC/SP1, GH-TRE and PR/GR binding site. In further embodiments, the regulators comprise a 5' untranslated UCP3 gene exon. Frequently, the regulators may further comprising a UCP3 or non-UCP3 core promoter operatively joined to said mutant.

The invention also provides hybridization probes and replication/amplification primers having a hitherto novel UCP3 specific sequence contained in SEQ ID NO:1 or 2 (including its complement and analogs and complements thereof having the corresponding sequence, e.g . in RNA) and sufficient to effect specific hybridization thereto (i.e. specifically hybridize with the corresponding SEQ ID NO:1 or 2 in the presence of genomic DNA). Such primers or probes are at least 12, preferably at least 24, more preferably at least 36 bases in length.

The invention also provides cells and vectors comprising the disclosed UCP3 regulators, including cells comprising such regulators operably linked to non-UCP3 gene. Such cells find used in the disclosed methods for identifying agents which regulate the activity of a UCP3 promoter. In an exemplary such method, the cells are contacted with a candidate agent, under conditions wherein, but for the presence of said agent, the gene exhibits a first expression; detecting the presence of a second expression of the gene, wherein a difference between said first and said second expression indicates said agent regulates the activity of a UCP3 gene promoter.

The invention also provides other assays for transcriptional regulators including transcription complex formation assays. An exemplary such assay involves combining a DNA comprising a disclosed regulator with a transcription factor and a candidate agent, under conditions wherein, but for the presence of said agent, the regulator and transcription factor form a first association; detecting the presence of a second association of the regulator and transcription factor, wherein a difference between the first and second associations indicates the agent modulates the association of a UCP3 promoter and transcription factor. The subject nucleic acid regulators also find a variety of other applications, including uses in diagnosis. In particular, hybridization probes and PCR primers derived from the disclosed promoters are used to identify genetic mutations in samples comprising a UCP3 gene.

DETAILED DESCRIPTION OF THE INVENTION

Figure 1:
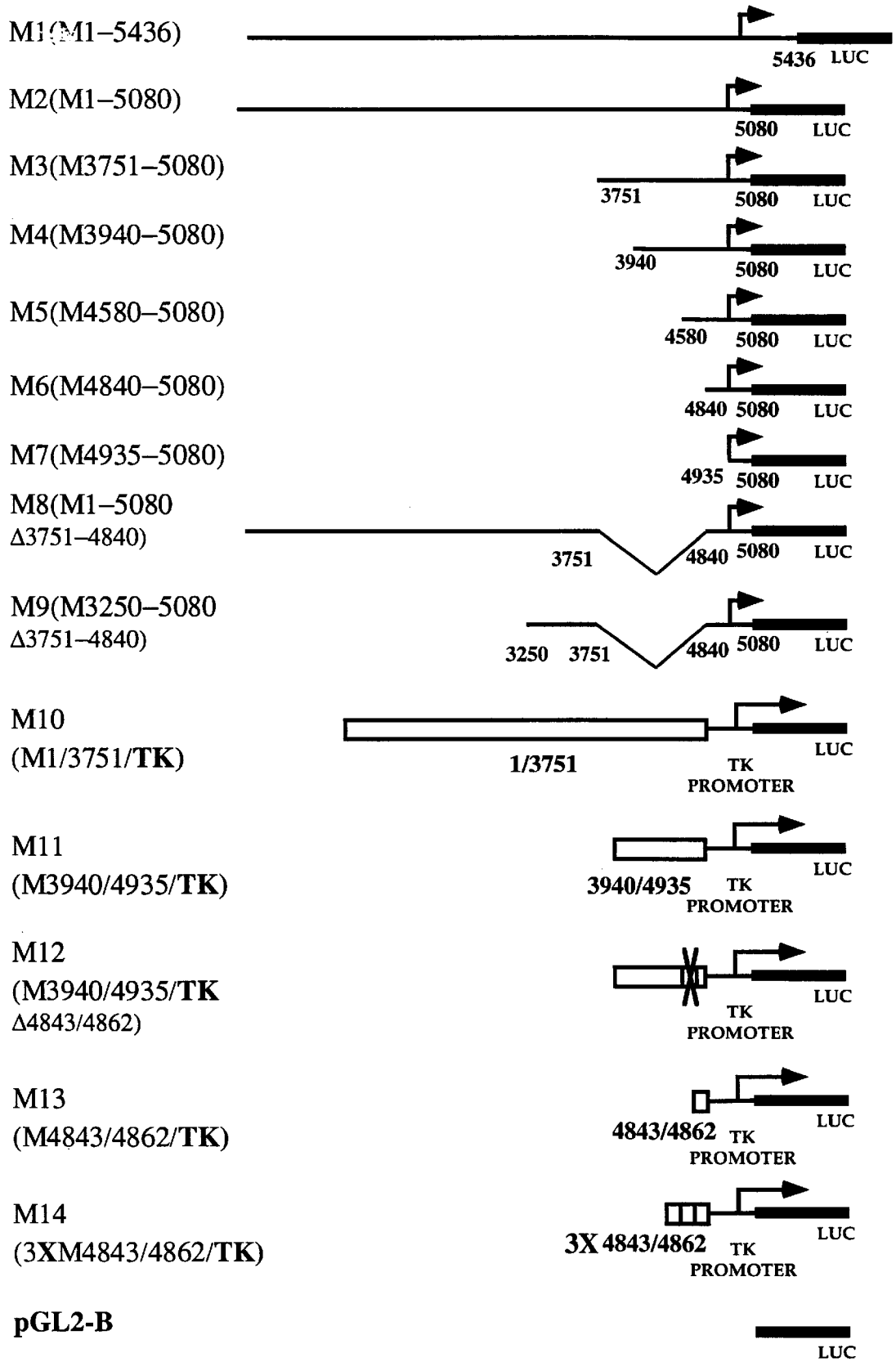
FIG. 1. Diagram of mUCP3 promoter constructs driving expression of luciferase enzymatic activity in $CaPO_4$ transfected HeLa cells. Cells are harvested 18 hrs post transfection and assayed for luciferase.

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or 2, or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is sometimes advantageous to use nucleic acids comprising other bases or nucleotide analogs to provide modified stability, etc.

The subject nucleic acids find a wide variety of applications including use as hybridization probes, PCR primers, therapeutic nucleic acids, etc.; use in detecting the presence of UCP3 genes and gene transcripts, in detecting or amplifying nucleic acids encoding additional UCP3 homologs and structural analogs, in gene therapy applications and in a variety of screening assays.

In diagnosis, UCP3-promoter specific hybridization probes find use in identifying wild-type and mutant UCP3 alleles in clinical and laboratory samples. Mutant alleles are used to generate allele-specific oligonucleotide (ASO) probes for high-throughput clinical diagnoses. In therapy, therapeutic UCP3 nucleic acids are used to modulate cellular expression or intracellular concentration or availability of active UCP3. For example, UCP3 nucleic acids are used to modulate cellular expression or intracellular concentration or availability of active UCP3 protein. UCP3 inhibitory nucleic acids are typically antisense: single-stranded sequences comprising complements of the disclosed natural UCP3 transcript sequences, particularly the untranslated exon 1. Antisense modulation of the expression of a given UCP3 protein may employ antisense nucleic acids operably linked to gene regulatory sequences. Cell are transfected with a vector comprising a UCP3 sequence with a promoter sequence oriented such that transcription of the gene yields an antisense transcript capable of binding to endogenous UCP3 encoding mRNA. Alternatively, single-stranded antisense nucleic acids that bind to genomic DNA or mRNA encoding UCP3 protein may be administered to the target cell, in or temporarily isolated from a host, at a concentration that results in a substantial reduction in expression of the targeted protein. An enhancement in UCP3 expression is effected by introducing into the targeted cell type UCP3 nucleic acids which increase the functional expression of the corresponding gene products. Such nucleic acids may be UCP3 expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying pharmacological agents or lead compounds for agents active at the level of UCP3 gene transcription. The methods are amenable to automated, cost-effective high throughput screening of chemical libraries for lead compounds. A wide variety of assays for transcriptional regulators are provided including cell-based transcription assays, promoter-protein binding assays, etc. For example, the disclosed luciferase reporter constructs are used to transfect cells such as HeLa cells for cell-based transcription assays. Specifically, HeLa cells are plated onto microtiter plates and used to screen libraries of candidate agents for lead compounds which modulate the transcriptional regulation of the UCP3 gene promoter, as monitored by luciferase expression. An exemplary promoter-protein binding assay is described below. The following examples, exemplary promoter deletion mutants and screening assays are offered by way of illustration and not by way of limitation.

EXAMPLES

Transfection of Cultured HeLa Cells

Transient transfections were carried out using cultured HeLa cells by calcium phosphate precipitation. 5 μg of promoter-luciferase plasmid DNA were co-transfected with either 1 μg of pMSV expression vector or 1 μg of pMSV-TR expression vector. Samples were co-precipitated with 2 μg of salmon sperm DNA and 0.2 μg of a β-galactosidase internal control expression vector, then applied atop adherent HeLa cells in 6 well tissue culture plates. After 16 hr cells were washed in phosphate buffered saline and refed with fresh DMEM/F12 culture medium supplemented with 10% fetal bovine serum. After an additional 24 hr cells were harvested, lysed and assayed for luciferase and β-galactosidase enzymatic activity according to manufacturer's recommendations (Promega).

Isolation of Human and Mouse UCP3 Genomic Clones

Genomic clones containing the promoter region, the first exon and the remaining 5' untranslated region of the human and mouse UCP3 gene weres obtained by hybridization screening of bacteriophage 1 libraries using PCR amplified probes derived from hUCP3 and mUCP3 encoding sequences. The clones were further confirmed by rehybridization using PCR probes derived from 5' untranslated region sequence, which were obtained from RACE PCR amplification. Genomic clones were subcloned into pBluescript KSII (Stratagene), and then sequenced using an Applied Biosystems DNA sequencer. The promoter sequences were subjected to BLAST search on the NCBI server; no homologies to any known sequence were found. Indentically conserved oligonucleotides (discernable from alignment of SEQ ID NOS:1 and 2) are used in primers and probes for UCP3 genes.

The DNA sequence of the first untranslated exon and upstream DNA of the human and mouse UCP3 genes are shown in SEQ ID NOS:1 and 2, respectively. A number of transcription factor binding sites, splice sites and transcriptional start sites for the human and mouse genes are are shown in Tables I and II, respectively.

TABLE I

Human UCP3 gene transcriptional start, splice and factor binding sites.

| SITE | SEQ ID NO:1 nucleotides | SITE | SEQ ID NO:1 nucleotides |
|---|---|---|---|
| c-Myc | 1132–1138 | HiNF-A | 1115–1121 |
| IBP-1 | 1355–1360 | AP-2 | 961–968 |
| C/EBP | 1006–1013 | HC3 | 269–274 |
| NF-IL6 | 266–274 | GCF | 396–403 |
| GH-CSE2 | 843–849 | GH-CSE1 | 853–859 |
| HNF5 | 566–572 | GR | 602–1607 |
| AP-I | 1944–1950 | AP-2 | 1525–1532 |
| START SITE | 1461, 1399–1548 | INTRON I | 1549–2000 |

TABLE II

Mouse UCP3 gene transcriptional start, splice and factor binding sites.

| SITE | SEQ ID NO:2 nucleotides | SITE | SEQ ID NO:2 nucleotides |
|---|---|---|---|
| c-Myc | 4716–4722 | MyoD | 4675–4681 |
| gamma IRE | 4851–4859 | NF-kB | 4701–4712 |
| PR | 4861–4869 | NFIL6 | 4405–4414 |
| C/EBP | 4287–4295 | MyoD | 3929–3935 |
| SRF | 3915–3925 | AP-2 | 3706–3714 |
| NF-IL6 | 3204–3214 | p53 | 3062–3072 |
| HiNF-A | 2968–2976 | b-α-tabuli | 2801–2810 |
| AP-1 | 2410–2418 | GH-CSE1 | 1974–1982 |
| Insulin-Responsive | 1152–1159 | CREB | 791–799 |
| AP-2 | 293–301 | GcF | 4996–5003 |
| ApoE-B2 | 5381–5393 | START | 4935–4948 |
| EXON | 4935–5080 | INTRON | 5081–5436 |

Deletion Mutant construction and Activity Analysis

The promoter activity of the 5' flanking region of human UCP3 gene and a variety of deletion mutants thereof are conveniently screened in a transient transfection assay using mammalian cell lines. An exemplary assay is the HeLa-cell based luciferase reporter assay of FIGS. 1 and 2. Selected promoter deletions are amplified by PCR using targeting primers. Amplification primer pairs for exemplified deletions are as follows:

| Tagged/untagged endonuclease site | Nucleotide Sequence |
|---|---|
| att-Mlu1 | ATTACGCGT |
| att-HindIII | ATTAAGCTT |
| att-EcoR1 | ATTGAATTC |
| Mlu1 (core) | CGCG |

H1: att-Mlul—(SEQ ID NO:1, nucleotides 1–20) att-Hind III (reverse compliment of SEQ ID NO:1, nucleotides 1981–2000)

H2 att-Mlul—(SEQ ID NO:1, nucleotides 1–20) att-Hind III—(reverse compliment of SEQ ID NO:1, nucleotides 1529–1548)

H3 att-Mlul—(SEQ ID NO:1, nucleotides 200–219) att-Hind III—(reverse compliment of SEQ ID NO:1, nucleotides 1529–1548)

H4 —(SEQ ID NO:1, nucleotides 1091–1110) att-Hind III—(reverse compliment of SEQ ID NO:1, nucleotides 1529–1548)

H5 att-Mlul (SEQ ID NO:1, nucleotides 1286–1306) att-HIND III—(reverse compliment of SEQ ID NO:1, nucleotides 1529–1548)

H6 att-Mlul—(SEQ ID NO:1, nucleotides 1462–1482) att-Hind III—(reverse compliment of SEQ ID NO:1, nucleotides 1529–1548)

H7 att-Mlul—(SEQ ID NO:1, nucleotides 1–20) att-Hind III—(reverse compliment of SEQ ID NO:1, nucleotides 1068–1090)

H8 att-Mlul—(SEQ ID NO:1, nucleotides 1286–1306) att-Hind III—(reverse compliment of SEQ ID NO:1, nucleotides 1441–1461)

M1 att-Mlul—(SEQ ID NO:2, nucleotides 1–25) att-Hind III—(reverse compliment of SEQ ID NO:2, nucleotides 5411–5436)

M2 att-Mlul—(SEQ ID NO:2, nucleotides 1–25) att-Hind III—(reverse compliment of SEQ ID NO:2, nucleotides 5054–5080)

M3 att-Mlul—(SEQ ID NO:2, nucleotides 3751–3778) att-Hind III—(reverse compliment of SEQ ID NO:2, nucleotides 5054–5080)

M4 att-Mlul—(SEQ ID NO:2, nucleotides 3940–3967) att-Hind III—(reverse compliment of SEQ ID NO:2, nucleotides 5054–5080)

M5 att-Mlul—(SEQ ID NO:2, nucleotides 4581–4612) att-Hind III—(reverse compliment of SEQ ID NO.2, nucleotides 5054–5080)

M6 att-Mlul—(SEQ ID NO:2, nucleotides 4840–4867) att-Hind III—(reverse compliment of SEQ ID NO 2, nucleotides 5054–5080)

M7 att-Mlul—(SEQ ID NO:2, nucleotides 4930–4958) att-Hind III—(reverse compliment of SEQ ID NO:2, nucleotides 5054–5080)

The deletions may be recombined in any desired variation. For example internal deletions are readily prepared by amplifying both 5' and 3' deletions followed by ligation, Alternatively, a UCP3 promoter deletion may be fused with non-UCP3 promoter element(s) to form heterohybrid promoters. Internal deletions and heterohybrid constructs are exemplified as follows: p1 M8 1a&1b pair; 2a&b pair 1a. att-Mlul—(SEQ ID NO:2, nucleotides 1–25)

1b, att-EcoRl—(reverse compliment of SEQ ID NO:2, nucleotides 3727–3751)

2a. att-EcoRl—(SEQ ID NO02, nucleotides 4840–4870)

2b. att-Hind III—(reverse compliment of SEQ ID NO:2, nucleotides 5054–5080)

M9 1a. att-Mlul—(SEQ ID NO:2, nucleotides 3249–3274)

1b. att-EcoRl—(reverse compliment of SEQ ID NO:2, nucleotides 3727–3751)

2a. att-EcoRl—(SEQ ID NO:2, nucleotides 4840–4870)

2b. att-Hind III—(reverse compliment of SEQ ID NO:2, nucleotides 5054–5080)

M10 att-Mlul—(SEQ ID NO:2, nucleotides 1–25) att-EcoR1—(reverse compliment of SEQ ID NO:2, nucleotides 3727–3751)

M11 att-Mlul—(SEQ ID NO:2, nucleotides 3940–3967) att-EcoRl—(reverse compliment of SEQ ID NO:2, nucleotides 4910–4935)

M12 1a. att-Mlul—(SEQ ID NO:2, nucleotides 3940–3967)

1b. att-EcoRl—(reverse compliment of SEQ ID NO:2, nucleotides 4823–4842)

2a. att-EcoRl—(SEQ ID NO:2, nucleotides 4863–4887)

2b. att-EcoRl—(reverse compliment of SEQ ID NO:2, nucleotides 4910–4935)

M13 &M14—Oligo anealing no PCR

Mlul—(SEQ ID NO.2, nucleotides 4843–4862)

Mlul—(reverse compliment of SEQ ID NO:2, nucleotides 4843–4862)

Figure 2:
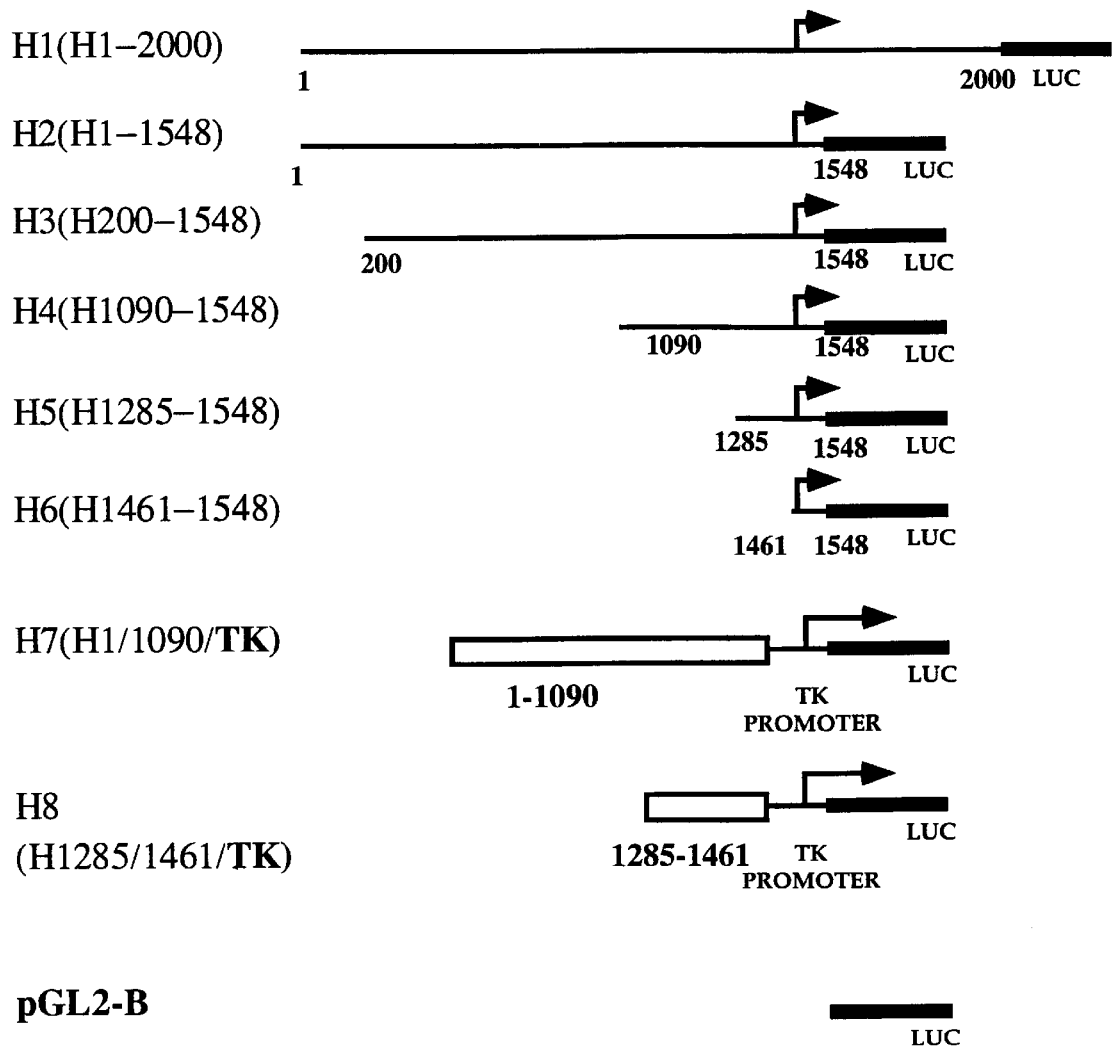
FIG. 2. Diagram of hUCP3 promoter constructs driving expression of luciferase enzymatic activity in $CaPO_4$ transfected HeLa cells. Cells are harvested 18 hrs post transfection and assayed for luciferase.

The PCR fragments are restriction enzyme digested by Mlul and HindIII, and then subcloned into Mlul and HindIII sites of pGL-2B or pGL-2P (Promega). Transient transfections are carried out using cultued HeLa cells by calcium phosphate precitation method. After 40 hours, cells are harvested, lysed and assayed for luciferase activity. Exemplary mutants are shown to a range of transcriptional activity (FIGS. 1, 2).

Protocol for AP—UCP3Gene Promote Binding Assay

A. Reagents

Neutralite Avidin: 20 µg/ml in PBS.

Blocking buffer: 5% BSA, 0.5% Tween 20 in PBS; 1 hr, RT.

Assay Buffer: 100 mM KCI, 20 mM HEPES pH 7.6, 0.25 mM EDTA, 1% glycerol, 0.5 % NP-40, 50 mM BME, 1 mg/ml BSA, cocktail of protease inhibitors.

$^{33}$AP-2 10×stock: $10^{-6}$–$10^{-8}$M "cold" AP-2 supplemented with 200,000–250,000 cpm of labeled AP-2 (Beckman counter). Place in the 4° C. microfridge during screening.

Potease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock, (specific biotinylated). Biotinylated oligo at 17 pmole/µl, UCP3 gene promoter containing AP-2 site: (BIOTIN)—(SEQ ID NO:1, bases 950–970).

B. Preparation of Assay Plates

Coat with 120 μl of stock N-Avidin per well overnight at 4° C.

Wash 2× with 200 μl PBS.

Block with 150 μl of blocking buffer.

Wash 2× with 200 μl PBS.

C. Assay

Add 40 μl assay buffer/well.

Add 10 μl compound or extract.

Add 10 μl $^{33}$P-AP-2 (20,000–25,000 cpm/0.1–10 pmoles/well=$10^{-9}$–$10^{-7}$M final concentration).

Shake at 25° C. for 15 min.

Incubate additional 45 min. at 25° C.

Add 40 μl oligo mixture (1.0 pmoles/40 μl in assay buffer with 1 ng of ss-DNA)

Incubate 1 hr at RT.

Stop the reaction by washing 4× with 200 μl PBS.

Add 150 μl scintillation cocktail

Count in Topcount.

D. Controls for all Assays (located on each plate)

a. Non-specific binding (no oligo added)

b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid composing SEQ ID NO:1 or 2, or a fragment thereof at least 50 bp in length comprising at least one sequence selected from the group consisting of SEQ ID NO:1, nucleotides 411–460; SEQ ID NO:1, nucleotides 461–510; SEQ ID NO:1, nucleotides 401–563; SEQ ID NO:1, nucleotides 319–326; SEQ ID NO:1, nucleotides 98–104; SEQ ID NO:1, nucleotides 49–56; SEQ ID NO:1, nucleotides 49–104; SEQ ID NO:1, nucleotides 547–554; SEQ ID NO:1, nucleotides 1–1548; SEQ ID NO:1, nucleotides 200–1548; SEQ ID NO:1, nucleotides 1090–1548; SEQ ID NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; SEQ ID NO:2, nucleotides 3940–4935; and SEQ ID NO:2, nucleotides 4843–4862.

2. The nucleic acid of claim 1 comprising at least one binding site from Table 2 or 3.

3. The nucleic acid of claim 1 operatively joined to a non-UCP3 core promoter.

4. The nucleic acid of claim 1 comprising a 5' untranslated UCP3 gene exon.

5. A cell comprising the nucleic acid of claim 1 operably linked to a non-UCP3 gene.

6. The nucleic acid of claim 1 comprising at least one sequence selected from the group consisting of SEQ ID NO:1, nucleotides 411–460; SEQ ID NO:1, nucleotides 461–510; SEQ ID NO:1, nucleotides 401–563; SEQ ID NO:1, nucleotides 49–104; SEQ ID NO:1, nucleotides 1–1548; SEQ ID NO:1, nucleotides 200–1548; SEQ ID NO:1, nucleotides 1090–1548; SEQ ID NO:1, nucleotides 1285–1548; SEQ ID NO:1, nucleotides 1–1090; SEQ ID NO:1, nucleotides 1285–1461; SEQ ID NO:2, nucleotides 1–5080; SEQ ID NO:2, nucleotides 3751–5080; SEQ ID NO,2, nucleotides 3940–5080; SEQ ID NO:2, nucleotides 4580–5080; SEQ ID NO:2, nucleotides 4840–5080; SEQ ID NO:2, nucleotides 1–3571; and SEQ ID NO:2, nucleotides 3940–4935.

7. The nucleic acid of claim 6 comprising at least one binding site from Table 2 or 3.

8. The nucleic acid of claim 6 operatively joined to a non-UCP3 core promoter.

9. The nucleic acid of claim 6 comprising a 5' untranslated UCP3 gene exon.

10. A cell comprising the nucleic acid of claim 6 operably linked to a non-UCP3 gene.

11. An isolated nucleic acid comprising SEQ ID NO:1 or 2, or a fragment thereof at least 50 bp in length comprising at least one sequence selected from the group consisting of SEQ ID NO 1, nucleotides 401–563; SEQ ID NO:1, nucleotides 1–1548; SEQ ID NO:1, nucleotides 200–1548; SEQ ID NO: 1, nucleotides 1–1090; SEQ ID NO:2, nucleotides 1–5080; SEQ ID NO:2, nucleotides 3751–5080; SEQ ID NO:2, nucleotides 3940–5080; SEQ ID NO:2, nucleotides 4580–5080; SEQ ID NO:2, nucleotides 4840–5080; SEQ ID NO:2, nucleotides 1–3571; and SEQ ID NO:2, nucleotides 3940–4935.

12. The nucleic acid of claim 11 comprising at least one binding site from Table 2 or 3.

13. The nucleic acid of claim 11 operatively joined to a non-UCP3 core promoter.

14. The nucleic acid of claim 11 comprising a 5' untranslated UCP3 gene exon.

15. A cell comprising the nucleic acid of claim 11 operably linked to a non-UCP3 gene.

16. An isolated nucleic acid comprising SEQ ID NO:1 or 2.

17. The nucleic acid of claim 16 operatively joined to a non-UCP3 core promoter.

18. The nucleic acid of claim 16 comprising a 5' untranslated UCP3 gene exon.

19. A cell comprising the nucleic acid of claim 16 operably linked to a non-UCP3 gene.

* * * * *